United States Patent
Kato et al.

(10) Patent No.: US 10,456,504 B2
(45) Date of Patent: Oct. 29, 2019

(54) ACICULAR BODY

(71) Applicant: TOPPAN PRINTING CO., LTD., Taito-ku (JP)

(72) Inventors: Hiroyuki Kato, Taito-ku (JP); Takako Yamamoto, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 711 days.

(21) Appl. No.: 15/003,457

(22) Filed: Jan. 21, 2016

(65) Prior Publication Data

US 2016/0213819 A1  Jul. 28, 2016

Related U.S. Application Data

(63) Continuation of application No. PCT/JP2014/069290, filed on Jul. 22, 2014.

(30) Foreign Application Priority Data

Jul. 22, 2013 (JP) .................. 2013-151797

(51) Int. Cl.
*A61L 31/04* (2006.01)
*A61M 37/00* (2006.01)
*A61M 5/00* (2006.01)

(52) U.S. Cl.
CPC ............ *A61L 31/042* (2013.01); *A61M 5/00* (2013.01); *A61M 37/0015* (2013.01); *A61M 2037/0053* (2013.01)

(58) Field of Classification Search
CPC ............ A61M 5/00; A61M 2037/0023; A61M 2037/003; A61M 2037/0038; A61M 2037/0046; A61M 2037/0053; A61M 2037/0061; A61M 37/0015; A61M 37/00; A61M 2205/583; A61M 2205/584; A61B 17/205; A61K 9/0021

See application file for complete search history.

(56) References Cited

U.S. PATENT DOCUMENTS

| | | | |
|---|---|---|---|
| 2008/0108958 A1* | 5/2008 | Carter | A61M 37/0015 604/272 |
| 2008/0200883 A1 | 8/2008 | Tomono | |
| 2008/0208134 A1 | 8/2008 | Tomono | |

(Continued)

FOREIGN PATENT DOCUMENTS

| | | |
|---|---|---|
| JP | 48-93192 A | 12/1973 |
| JP | 2009-273772 A | 11/2009 |

(Continued)

OTHER PUBLICATIONS

English Translation of JP2009273772.*

(Continued)

*Primary Examiner* — Kami A Bosworth
*Assistant Examiner* — Alexandra Lalonde
(74) *Attorney, Agent, or Firm* — Oblon, McClelland, Maier & Neustadt, L.L.P.

(57) ABSTRACT

An acicular body includes a support plate having a brightness of 5.0 or less, and a needle disposed on the support plate. The needle includes a tip formed to pierce a skin and a light transmission area which is located in an area including the tip and has a total light transmittance of 20% or more.

20 Claims, 8 Drawing Sheets

(56) References Cited

U.S. PATENT DOCUMENTS

| | | | | |
|---|---|---|---|---|
| 2008/0269685 A1* | 10/2008 | Singh | ........... | A61K 9/0021 604/173 |
| 2008/0287858 A1* | 11/2008 | Duan | ........... | A61M 37/0015 604/21 |
| 2009/0131887 A1 | 5/2009 | Shiomitsu et al. | | |
| 2009/0143749 A1 | 6/2009 | Sugimura et al. | | |
| 2009/0292254 A1 | 11/2009 | Tomono | | |
| 2009/0292255 A1 | 11/2009 | Tomono | | |
| 2010/0185162 A1 | 7/2010 | Shiomitsu et al. | | |
| 2010/0198169 A1 | 8/2010 | Sugimura et al. | | |
| 2011/0195124 A1 | 8/2011 | Jin | | |
| 2012/0041412 A1* | 2/2012 | Roth | ........... | A61M 25/10 604/500 |
| 2012/0265145 A1 | 10/2012 | Mefti et al. | | |
| 2012/0277697 A1* | 11/2012 | Haghgooie | ........... | A61B 5/1411 604/319 |
| 2013/0030374 A1 | 1/2013 | Sugimura et al. | | |
| 2013/0140267 A1 | 6/2013 | Shiomitsu et al. | | |
| 2015/0209563 A1* | 7/2015 | Amir | ........... | A61K 9/0021 604/46 |
| 2016/0015952 A1* | 1/2016 | Omachi | ........... | A61M 37/0015 604/46 |

FOREIGN PATENT DOCUMENTS

| | | | | |
|---|---|---|---|---|
| JP | 2009273772 A | * | 11/2009 | ........ A61M 37/0015 |
| JP | 2009-297478 A | | 12/2009 | |
| JP | 2010-75374 A | | 4/2010 | |
| JP | 2012-505164 A | | 3/2012 | |
| JP | 2013-515524 A | | 5/2013 | |
| WO | WO 2008/004597 A1 | | 1/2008 | |
| WO | WO 2008/013282 A1 | | 1/2008 | |
| WO | WO 2008/020632 A1 | | 2/2008 | |

OTHER PUBLICATIONS

International Search Report dated Oct. 7, 2014 in PCT/JP2014/069290, filed Jul. 22, 2014.

Kansai Bureau of Economy, Trade and Industry, "Yakubutsu Sentanbu Tosai-gata Shinki Microneedle no Kaihatsu to sono Ikumo Seizai eno Oyo", [online], 2012.03, [retrieval date Sep. 29, 2014], Internet <URL: http://www.chusho.meti.go.jp/keiei/sapoin/portal/seika/2010/22h-73.pdf>.

Office Action dated Mar. 29, 2016 in Korean Patent Application No. 10-2016-7002840 (with English language translation).

* cited by examiner

ACICULAR BODY

CROSS-REFERENCE TO RELATED APPLICATIONS

The present application is a continuation of International Application No. PCT/JP2014/069290, filed Jul. 22, 2014, which is based upon and claims the benefits of priority to Japanese Application No. 2013-151797, filed Jul. 22, 2013. The entire contents of these applications are incorporated herein by reference.

BACKGROUND OF THE INVENTION

Field of the Invention

The present invention relates to an acicular body, and more specifically, a fine acicular body which is applied onto the skin so as to pierce the skin.

Discussion of the Background

A percutaneous absorption method, which is a method for allowing a substance such as drug to penetrate through the skin to be delivered into the body is used as a convenient way of painless administration of the substance to be delivered.

In the field of percutaneous administration using a percutaneous absorption method, a technique has been proposed in which an acicular body having a needle which is sized in the order of micro-meters is used to pierce the skin, thereby administering a substance such as a drug into the skin (see PTL 1).

A method for manufacturing the acicular body has been proposed, in which an original plate is manufactured by machine processing, the original plate is used to fabricate a transfer plate, and the transfer plate is used for transfer molding (see PTL 2).

Another method for manufacturing the acicular body has been proposed, in which an original plate is manufactured by etching, the original plate is used to fabricate a transfer plate, and the transfer plate is used for transfer molding (see PTL 3).

The acicular body is preferably made of a material that is harmless to the body even if a broken piece of the acicular body remains in the body. Accordingly, biocompatible materials such as chitin and chitosan are proposed as materials for the acicular body (see PTL 4).

Further, when the acicular body is used for piercing the skin, it is preferable to use an adhesive material in order to prevent the acicular body from falling off from the skin.

PLT 1: JP-A-S48-93192
PLT 2: WO 2008/013282
PLT 3: WO 2008/004597
PLT 4: WO 2008/020632

SUMMARY OF THE INVENTION

According to one aspect of the present invention, an acicular body includes a support plate having a brightness of 5.0 or less, and a needle formed on the support plate and including a tip formed to pierce a skin. The needle has a light transmission area located in an area including the tip, and the light transmission area has a total light transmittance of 20% or more.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
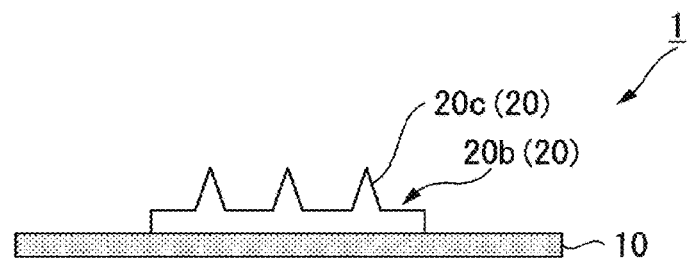
FIG. 1 is a schematic view which shows an acicular body according to one embodiment of the present invention.
Figure 2A:
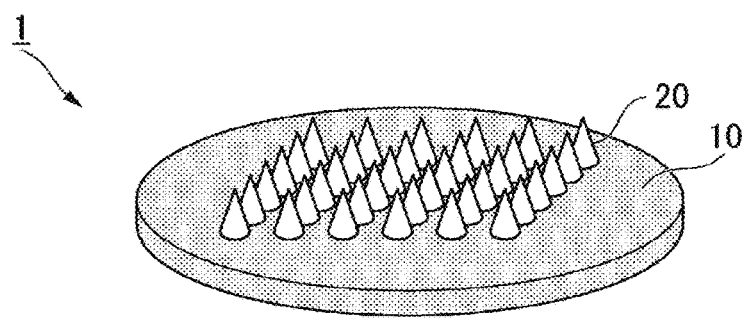
FIG. 2A is a perspective view which shows a modified example 1 of the acicular body according to one embodiment of the present invention.
Figure 2B:
FIG. 2B is a sectional view which shows the modified example 1 of the acicular body according to one embodiment of the present invention.

The embodiments will now be described with reference to the accompanying drawings, wherein like reference numerals designate corresponding or identical elements throughout the various drawings.

With reference to FIGS. 1 to 3B, an acicular body according to one embodiment of the present invention will be described. First, a configuration of the acicular body manufactured in the present embodiment will be described.

An acicular body 1 of the present embodiment includes a support plate (base) 10 and needles 20 (light transmission areas 20c) formed on the support plate 10.

The support plate 10 supports the needles 20 and may be formed by a film made of resin or the like. The material of the film member used for the support plate 10 is not specifically limited, and may be, for example, cellophane, polyethylene, polypropylene or polyimide.

The needle 20 is made of a material which dissolves after it is pierced into the skin. The needle 20 may be made of a material such as water-soluble polymer or disaccharide. The needle contains a desired substance to be delivered which is mixed or applied so that the substance to be delivered is percutaneously introduced in the body when the needle dissolves in the skin.

Water-soluble polymers which can be used as a material for the needle may include carboxymethyl cellulose (CMC), methylcellulose (MC), hydroxypropyl cellulose (HPC), hydroxypropyl methylcellulose (HPMC), polyvinyl alcohol (PVA), polyacrylic acid polymer, polyacrylamide (PAM), polyethylene oxide (PEO) and the like. Since the needle 20 is made of water-soluble polymer, a user can visually recognize that the needle disappears after the acicular body is applied. This improves the user's ease of use.

Disaccharides which can be used as a material for the needle may include sucrose, lactulose, lactose, maltose, trehalose, cellobiose and the like. Particularly, trehalose which is a disaccharide is preferably used. When a substance to be delivered is a protein, trehalose protects and stabilizes the protein since trehalose has a crystal structure similar to that of water.

In addition to that, starch, chitosan, as well as chitosan derivative such as chitosan succinamide can be used. Hereinafter, those may be collectively referred to as "needle material".

Among the above described needle material, chitosan, chitosan succinamide, HPC and CMC are particularly preferable as a material for needle since they are biologically highly safe. The material for needle in the acicular body of the present embodiment is not limited to a specific material and may be any material that dissolves after it is pierced into the skin.

Each needle 20 may be in any shape as long as it can pierce the skin, and may be selected from various shapes such as cone, pyramid, cylinder, prism and pencil-like shape (a shape having a column body and a cone-shaped tip portion).

A single needle 20 may be provided on the support plate 10, or alternatively, a plurality of needles 20 may stand closely together on the support plate 10. When a plurality of needles 20 stand, the needles 20 are preferably arranged in array. The term "array" as used herein means that the needles are arranged in a specific pattern such as a matrix arrangement, a close-packed arrangement, a concentric circle arrangement and a random arrangement.

Figure 3A:
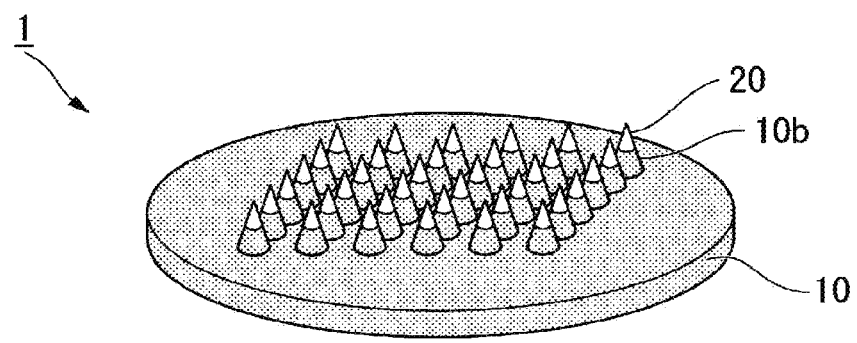
FIG. 3A is a perspective view which shows a modified example 2 of the acicular body according to one embodiment of the present invention.
Figure 3B:
FIG. 3B is a sectional view which shows the modified example 2 of the acicular body according to one embodiment of the present invention.

Further, FIG. 1 shows an example in which a plurality of needles 20 are integrally formed with a base portion 20b (needle) supported by the support plate 10. In the present embodiment, as shown in the modified example 1 of FIGS. 2A and 2B, the respective needles 20 may be independently formed on the support plate 10 instead of the needles 20 integrally formed with the base portion 20b. Further, as shown in the modified example 2 of FIGS. 3A and 3B, a plurality of needles 20 may be independently formed spaced from each other instead of the needles integrally formed with the base portion. In this configuration, as shown in FIGS. 3A and 3B, the support plate may include projections 10b formed at positions which correspond to the needles 20.

A hole may be formed at the tip of the needle 20. The hole may or may not penetrate through the support plate 10 in a thickness direction.

The needle 20 preferably has thickness and length suitable for creating a puncture hole into the skin. Specifically, the needle 20 preferably has a height H in the range of 10 μm to 1000 μm. The height H refers to a length from a surface of the support plate 10 to a tip of the needle 20.

The height H of the needle 20 may be determined within the above range depending on a desired depth of the puncture hole made by the acicular body piercing the skin.

For example, when a puncture hole made by the acicular body 1 piercing the skin is desired to be within the stratum corneum, the height H is preferably in the range of 10 μm to 300 μm, and more preferably, in the range of 30 μm to 200 μm.

Alternatively, when a puncture hole is desired to have a depth that penetrates through the stratum corneum and does not reach the nerve plexus, the height H is preferably in the range of 200 μm to 700 μm, more preferably, in the range of 200 μm to 500 μm, and further preferably, in the range of 200 μm to 300 μm.

When a puncture hole is desired to have a depth that reaches the dermis, the height H is preferably in the range of 200 μm to 500 μm.

Alternatively, when a puncture hole is desired to have a depth that reaches the epidermis, the height H is preferably in the range of 200 μm to 300 μm.

The needle 20 preferably has a width D in the range of 1 μm to 300 μm. The width D may be determined within the above range depending on a desired depth of the puncture hole made by the acicular body piercing the skin.

The width D is a maximum dimension of a portion of the needle which is in contact with the support plate when the needle is projected in parallel to a plane of the support plate 10. For example, when the needle is a conical or columnar shape, the width D is the diameter of the circular portion of the needle which is in contact with the support plate. When the needle is a regular quadrangular pyramid shape or regular quadrangular prism shape, the width D is the diagonal length of the square portion of the needle which is in contact with the support plate.

The needle 20 preferably has an aspect ratio in the range of 1 to 10. An aspect ratio A is defined as $A=H/D$, where H is a height and D is a width of the needle.

When the needle 20 has a tip angle of a cone-shaped portion and is used to penetrate through the stratum corneum, the tip angle θ of the needle is preferably in the range of 5 to 30 degrees, and more preferably, in the range of 10 to 20 degrees. The tip angle θ is a maximum angle (apex angle) when the needle 20 is projected in parallel to a plane of the support plate 10.

The substance to be delivered contained in the needle 20 may include various proteins, pharmacological active agents, cosmetic compositions and the like.

Pharmacological active agents may be selected as appropriate depending on the applications. For example, vaccines against influenza, analgesics for cancer patients, insulins, biologic agents, gene therapy agents, injection agents, oral agents or skin applying agents may be used. Since the acicular body according to the present invention pierces the skin, it can be applied to pharmacological active agents which need to be administered by subcutaneous injection besides the pharmacological active agents used for the conventional percutaneous administration. In particular, since injection agents such as vaccines can be administered painlessly by using the acicular body, the acicular body is suitable for use with children. Further, children have difficulty in swallowing an oral medication in the conventional way of administration. Since there is no need for swallowing a medication if the acicular body is used for drug administration, the acicular body is suitable for use with children.

The cosmetic compositions are compositions used for cosmetics or beauty products. For example, they may include moisturizing agents, coloring materials, fragrances, and biologically active substances that express beauty effects (beneficial effects for wrinkles, acne, stretch marks and the like, and mitigating effect on hair loss). When an aromatic material is used as a cosmetic composition, favorable fragrance can be added to the acicular body. This is suitable for use as a beauty product.

The needle 20 is formed to be transparent or translucent and has total light transmittance of 20% or more. Accordingly, the color of the support plate 10 can be visually observed via the needle 20.

The support plate 10 has a color having a brightness of 5.0 or less. As long as the support plate 10 has a brightness of 5.0 or less, hue and saturation are not specifically limited.

Since the total light transmittance of the needle 20 and the brightness of the support plate 10 in the acicular body 1 of the present embodiment are defined as described above, the needle 20 can be visually observed with ease when the needle 20 is seen from a position on the side of the needle 20 with the needle 20 overlapping the support plate 10 by virtue of the color of the support plate 10 which can be visually observed via the needle 20.

An example of manufacturing method of the acicular body 1 having the above configuration will be described.

First, an intaglio plate used for forming the needle is prepared. The original plate that defines the shapes of a plurality of needles 20 is manufactured. Then, the intaglio plate is manufactured by inverting the shapes of protrusions and recesses of the original plate. The original plate may be manufactured by a known method depending on the shapes of the needles, and may be manufactured by using micromachining technique. Examples of micromachining technique may include lithography, wet etching, dry etching, sandblasting, laser machining and precision machining. The intaglio plate may be manufactured by a known transfer molding method by using the original plate. For example, the intaglio plate made of Ni may be manufactured by Ni electroforming method, or the intaglio plate may be manufactured by transfer molding using melted resin.

With the procedure described above, the intaglio plate having the recesses which correspond to the needles 20 are formed.

Then, a needle-forming solution containing a needle material which is appropriately selected is prepared. The needle-forming solution preferably has a fluidity of such an extent that allows it to be suitably filled in the recesses of the intaglio plate by adjusting the amount of solute as appropriate, and the needle-forming solution may be in the form of gel. The total light transmittance of the needle is decided by adjusting the concentration and the like of the needle material in the needle-forming solution.

Then, the needle-forming solution is supplied onto the intaglio plate. A supplying method can be appropriately selected from known methods, taking into consideration the shape or dimensions of the intaglio plate. For example, methods such as spin coating method, method using a dispenser, casting method and ink-jet method can be used. Although the needle-forming solution may be supplied to the intaglio plate under an ordinary pressure, the needle-forming solution may also be supplied under a reduced pressure or vacuum pressure in order to perform more advantageous filling of the recesses. Preferably, the amount of the needle-forming solution is such an extent that allows it to cover all the recesses.

Then, the liquid component is removed from the needle-forming solution, and the needle-forming solution is solidified to form the needles.

This process can be performed by drying the needle-forming solution while holding the intaglio plate under a room temperature. Preferably, the needle-forming solution is heated and dried by heating the intaglio plate in order to shorten the required time. Heating method is not specifically limited, and, for example, a hotplate can be used so that the intaglio plate is placed thereon.

After the needles 20 are formed, the support plate 10 having a predetermined brightness is placed on the intaglio plate. An adhesive layer or the like is disposed on the surface of the support plate 10 so that the needles 20 are adhered to the support plate 10. When the support plate 10 is peeled off from an intaglio plate 30, the needles 20 are removed along with the support plate 10 from the intaglio plate 30. Accordingly, the acicular body 1 having the support plate 10 and the needles 20 are manufactured.

The intaglio plate 30 may be chemically dissolved instead of being peeled off as described above so as to separate the needles 20.

After completion of the acicular body 1, the acicular body 1 may be punched out to form a desired size and shape according to the application. A punching blade such as Thomson blade may be used for punching. Alternatively, the acicular body 1 may be punched out along with the intaglio plate before the support plate 10 is peeled off from the intaglio plate.

An adhesive may be applied on the periphery of the needles to provide an acicular body that can be applied as a patch on the skin or the like. An adhesive is preferably made of a material suitable for skin patching, and is further preferably made of a material that can be treated by a sterilization process.

Figure 4A:
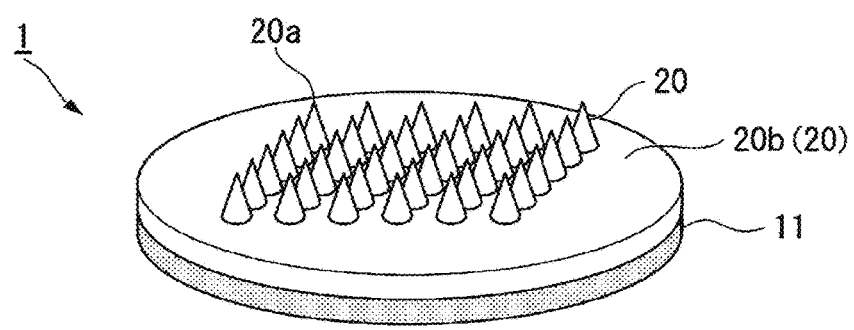
FIG. 4A is a perspective view which shows a modified example 3 of the acicular body according to one embodiment of the present invention.
Figure 4B:
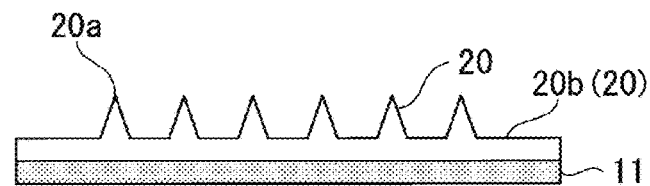
FIG. 4B is a sectional view which shows the modified example 3 of the acicular body according to one embodiment of the present invention.
Figure 5A:
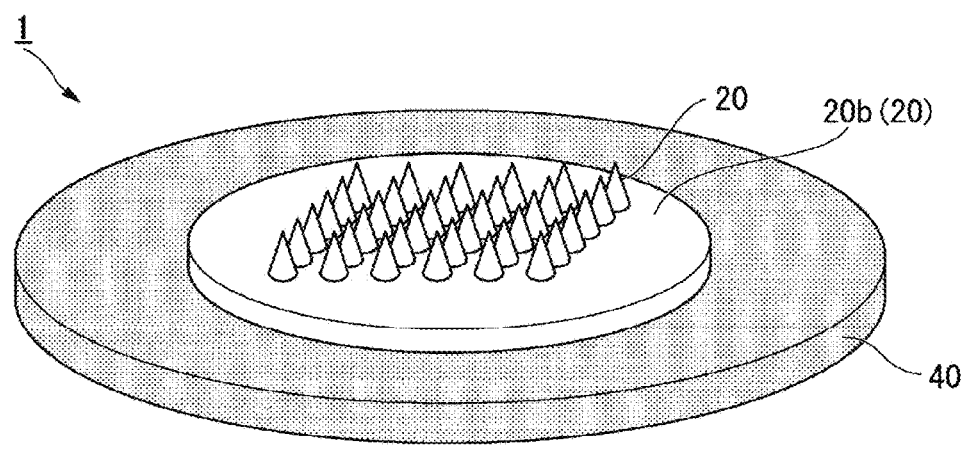
FIG. 5A is a perspective view which shows a modified example 4 of the acicular body according to one embodiment of the present invention.
Figure 5B:
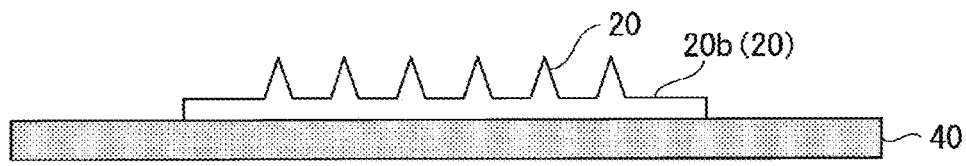
FIG. 5B is a sectional view which shows the modified example 4 of the acicular body according to one embodiment of the present invention.
Figure 6A:
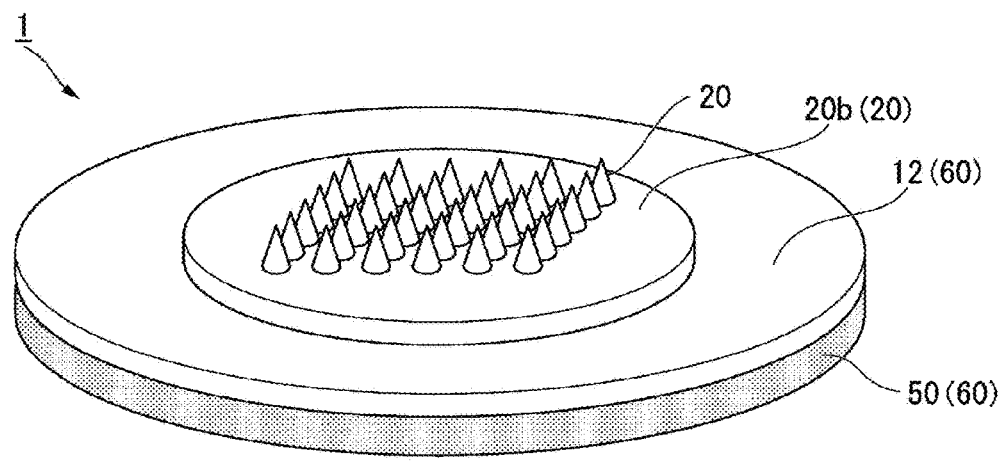
FIG. 6A is a perspective view which shows a modified example 5 of the acicular body according to one embodiment of the present invention.
Figure 6B:
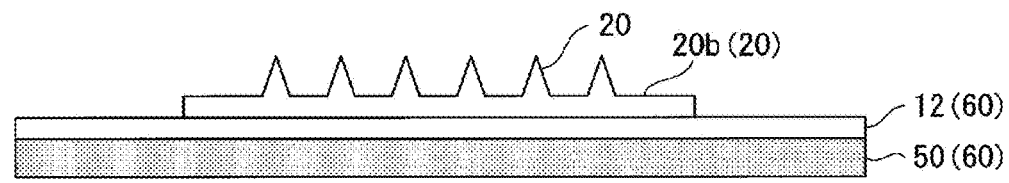
FIG. 6B is a sectional view which shows the modified example 5 of the acicular body according to one embodiment of the present invention.

The above manufacturing method is merely an example, and various modifications can be made. For example the support plate 11 as shown in FIGS. 4A and 4B may be formed by disposing a colored material which is made by adding a pigment to the needle-forming solution on the intaglio plate in the form of layer and solidifying it in the same manner as the needle 20, which does not need to use a colored film as the support plate. In this configuration, although part of the needle 20, for example, the base portion 20b may be colored as shown in FIGS. 4A and 4B, at least a portion having the tip 20a which is pierced into the skin (the light transmission area 20c including the tip 20a) has the above total light transmittance. Further, in the above embodiment, the acicular body is described as including the support plate formed by a colored film. Alternatively, as shown in FIGS. 5A and 5B, the transparent or translucent needles and the transparent or translucent base portion may be fixed on the colored support plate 40 such as an adhesive tape. Alternatively, as shown in FIGS. 6A and 6B, the transparent or translucent needles and the transparent or translucent base portion may be fixed on the support plate 60 such as an adhesive tape made up of a transparent adhesive layer 12 and a colored base material tape 50. In measurement of the brightness of the support plate 60 shown in FIGS. 6A and 6B, the brightness of the surface of the base material tape 50 which faces the transparent adhesive layer 12 may be measured.

According to the acicular body 1 of the present embodiment, since the total light transmittance of the needle 20 and the brightness of the support plate 10 are defined as described above, a user can visually observe the needle 20 disposed on the support plate 10 with ease. Accordingly, in applying the acicular body 1 on the skin, the needle 20 can be reliably applied at an intended position. Further, when the acicular body 1 is peeled off from the skin, the state of the needle 20, for example, whether the needle remains or not can be easily observed. As a result, the effect of the acicular body and the state of delivery of the substance to be delivered can be accurately recognized, thereby improving the effect and ease of use.

With reference to FIGS. 7A to 8D, the effect of the present invention will be described.

Figure 7A:
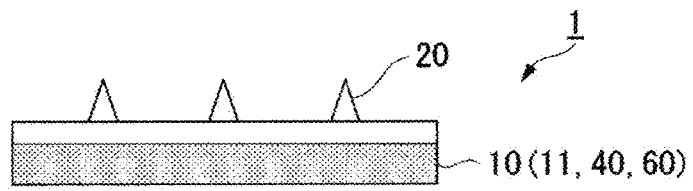
FIG. 7A is a side view of the acicular body according to one embodiment of the present invention before the acicular body is applied on the skin.
Figure 7B:
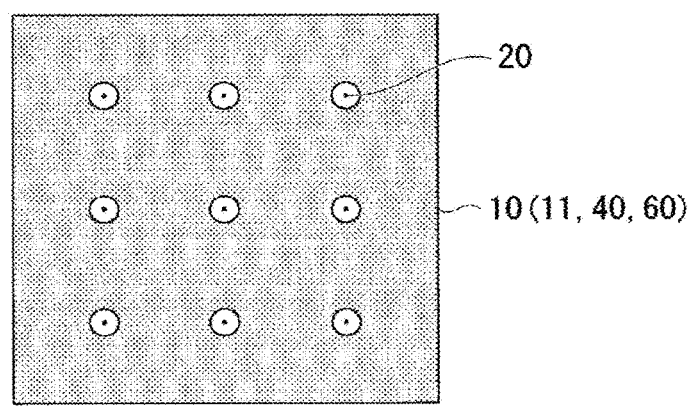
FIG. 7B is a top view of the acicular body according to one embodiment of the present invention before the acicular body is applied on the skin.
Figure 7C:
FIG. 7C is a side view of the acicular body according to one embodiment of the present invention after the acicular body is applied on the skin.
Figure 7D:
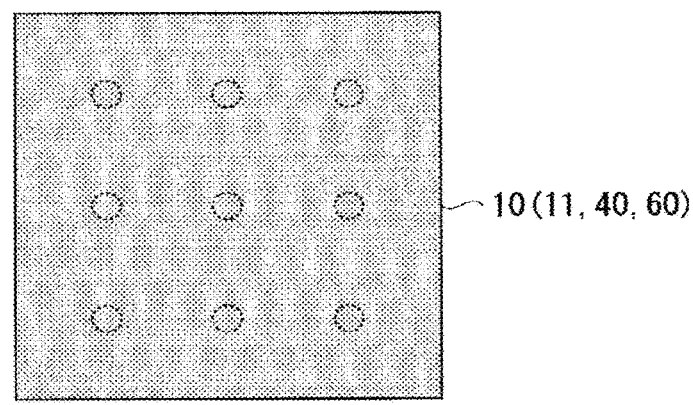
FIG. 7D is a top view of the acicular body according to one embodiment of the present invention after the acicular body is applied on the skin.

FIGS. 7A to 7D are explanatory views of the acicular body 1 according to the present embodiment. FIG. 7A is a side view of the acicular body before the acicular body is applied on the skin. FIG. 7B is a top view of the acicular body before the acicular body is applied on the skin. FIG. 7C is a side view of the acicular body after the acicular body is applied on the skin. FIG. 7D is a top view after the acicular body is applied on the skin.

While FIGS. 7A to 7D show the effect obtained by the acicular body according to one embodiment, the same effect can be obtained by a configuration which uses the above support plates 11, 40 and 60 instead of the support plate 10.

Figure 8A:
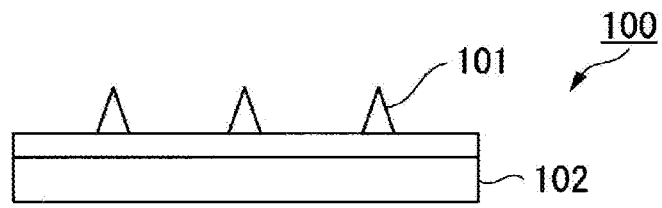
FIG. 8A is a side view of the conventional acicular body before the acicular body is applied on the skin.
Figure 8B:
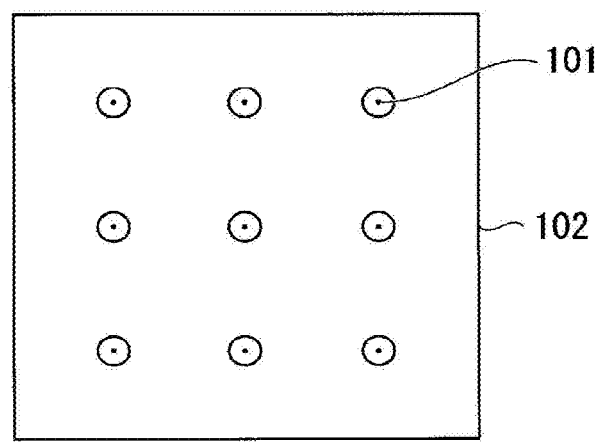
FIG. 8B is a top view of the conventional acicular body before the acicular body is applied on the skin.
Figure 8C:
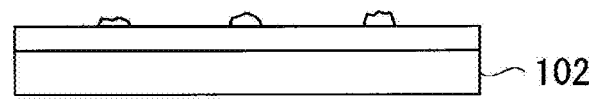
FIG. 8C is a side view of the conventional acicular body after the acicular body is applied on the skin.
Figure 8D:
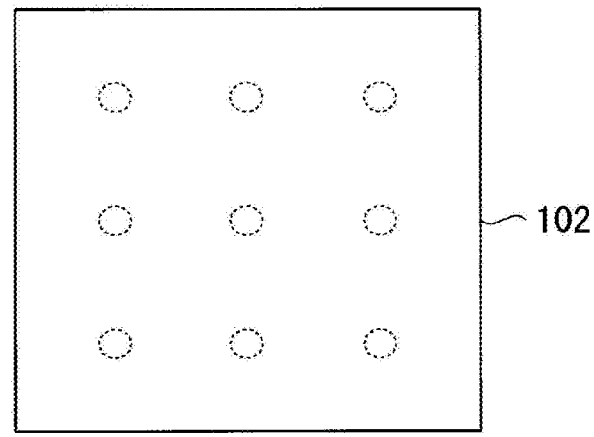
FIG. 8D is a top view of the conventional acicular body after the acicular body is applied on the skin.

FIGS. 8A to 8D are explanatory views of the conventional acicular body 100 which includes the needle 101 and the support plate 102. FIG. 8A is a side view of the acicular body before the acicular body is applied on the skin. FIG. 8B is a top view of the acicular body before the acicular body is applied on the skin. FIG. 8C is a side view of the acicular body after the acicular body is applied on the skin. FIG. 8D is a top view of the acicular body after the acicular body is applied on the skin.

According to the acicular body 1 of the present embodiment, a portion in the vicinity of the tip of the needle 20 can be seen brightly and clearly and is visually observed as shown in FIG. 7B. Accordingly, in applying the acicular body 1 on the skin, the needle 20 can be reliably applied at an intended position. Further, in observation of the acicular body after it is peeled off from the skin, the vicinity of the tip of the needle is not seen brightly any more as shown in FIG. 7D when the tip of the needle does not remain. Accordingly, a user can easily recognize that the needle tip has been dissolved by comparing the state before use which is shown in FIG. 7B and the state after being peeled off from the skin which is shown in FIG. 7D.

On the other hand, in the conventional acicular body, it is difficult to visually observe the portion in the vicinity of the tip of the needle 101 as shown in FIG. 8B compared with that shown in FIG. 7B. Accordingly, in the conventional acicular body, a user can not easily recognize that the needle tip has been dissolved since the difference between the state before use which is shown in FIG. 8B and the state after being peeled off from the skin which is shown in FIG. 8D is not readily understandable.

The acicular body of the present invention will be further described with reference to examples and comparative examples. However, the present invention is not limited in any way to these examples and comparative examples.

EXAMPLE 1

(Manufacturing of Intaglio Plate)

An original plate for the acicular body was formed by micromachining a silicon substrate so that 36 regular quadrangular pyramids (height: 150 μm, bottom: 60 μm×60 μm) were arrayed in a matrix of 6 rows by 6 columns with a pitch of 1 mm. The acicular body original plate was coated with a nickel film by plating in the thickness of 500 μm. Then, the silicon substrate was wet-etched with potassium hydroxide solution of weight percent concentration of 30% which was heated to 90° C. Accordingly, an intaglio plate made of nickel and having 36 recesses which correspond to the shape of the needles was manufactured.

(Preparation of Needle-forming Solution)

Chitosan succinamide, which was a chitosan derivative, was dissolved in water to prepare chitosan succinamide solution of weight percent concentration of 5% (5 wt %).

(Manufacturing of Needle)

A spin coating method was used to fill the recesses of the intaglio plate with the needle-forming solution. Then, the needle-forming solution was further supplied to such an extent that a layer was formed on the intaglio plate. The intaglio plate was heated at a temperature of 120° C. for a period of 10 minutes by using a heat source so that the needle-forming solution was dried and solidified. A hotplate was used as the heat source.

After the solidifying process, the needle-forming solution which was solidified in the form of layer was held and removed from the intaglio plate to manufacture a transparent needle.

The total light transmittance of the resultant needle measured in conformity with JIS K7105 (1981) "Testing methods for optical properties of plastics" was 80%.

(Manufacturing of Acicular Body)

An adhesive tape having an acrylic adhesive layer on the surface of a black polyvinyl chloride base material was provided as a support plate. The support plate and the manufactured needle were bonded to each other to form the acicular body of Example 1. In the above adhesive tape, the brightness L* of the surface having the adhesive layer was 1.5 (measured in conformity with JIS K5600-4-5 (1999) "Testing methods for paints—Part 4: Visual characteristics of film—Section 5: Colorimetry (Measurement)", the same applies hereinafter).

EXAMPLE 2

(Manufacturing of Intaglio Plate)

The same intaglio plate as that of Example 1 was used.

(Preparation of Needle-Forming Solution)

Hydroxypropyl cellulose was dissolved in water to prepare 10 wt % hydroxypropyl cellulose solution as a needle-forming solution.

(Manufacturing of Needle)

A spin coating method was used to fill the recesses of the intaglio plate with the needle-forming solution. Then, the intaglio plate was heated so that the needle-forming solution was dried and solidified.

After the solidifying process, the needle-forming solution which was solidified in the form of layer was held and removed from the intaglio plate to manufacture a translucent needle.

The total light transmittance of the resultant needle measured in conformity with JIS K7105 (1981) was 30%.

(Manufacturing of Acicular Body)

An adhesive tape having an acrylic adhesive layer on the surface of a black polyvinyl chloride base material was provided as a support plate. The support plate and the manufactured needle were bonded to each other to provide the acicular body of Example 2. In the above adhesive tape, the brightness L* of the surface having the adhesive layer was 1.5 (measured in conformity with JIS K5600-4-5 (1999)).

EXAMPLE 3

(Manufacturing of Intaglio Plate)

The same intaglio plate as that of Example 1 was used.

(Preparation of Needle-Forming Solution)

Hydroxypropyl cellulose and model antigen ovalbumin (OVA) were dissolved in water to prepare 10 wt % hydroxypropyl cellulose solution as a needle-forming solution.

(Manufacturing of Needle)

A spin coating method was used to fill the recesses of the intaglio plate with the needle-forming solution. Then, the intaglio plate was heated so that the needle-forming solution was dried and solidified.

After the solidifying process, the needle-forming solution which was solidified in the form of layer was held and removed from the intaglio plate to manufacture a translucent needle.

The total light transmittance of the resultant needle measured in conformity with JIS K7105 (1981) was 20%.

(Manufacturing of Acicular Body)

An adhesive tape having an acrylic adhesive layer on the surface of a blue polyvinyl chloride base material was provided as a support plate. The support plate and the manufactured needle were bonded to each other to provide the acicular body of Example 3. In the above adhesive tape, the brightness L* of the surface having the adhesive layer was 3.5 (measured in conformity with JIS K5600-4-5 (1999)).

EXAMPLE 4

(Manufacturing of Intaglio Plate)

The same intaglio plate as that of Example 1 was used.

(Preparation of Needle-forming Solution)

The same needle-forming solution (chitosan succinamide solution) as that of Example 1 was used.

(Manufacturing of Needle)

The needle was formed in the same manner as Example 1.

The total light transmittance of the resultant needle measured in conformity with JIS K7105 (1981) was 80%.

(Manufacturing of Acicular Body)

An adhesive tape having an acrylic adhesive layer on the surface of a dark brown polyvinyl chloride base material was provided as a support plate. The support plate and the manufactured needle were bonded to each other to provide the acicular body of Example 4. In the above adhesive tape, the brightness L* of the surface having the adhesive layer was 2.0 (measured in conformity with JIS K5600-4-5 (1999)).

EXAMPLE 5

(Manufacturing of Intaglio Plate)

The same intaglio plate as that of Example 1 was used.

(Preparation of Needle-Forming Solution)

The same needle-forming solution (chitosan succinamide solution) as that of Example 1 was used.

(Manufacturing of Needle)

The needle was formed in the same manner as Example 1.

The total light transmittance of the resultant needle measured in conformity with JIS K7105 (1981) was 80%.

(Manufacturing of Acicular Body)

An adhesive tape having an acrylic adhesive layer on the surface of a red polyvinyl chloride base material was provided as a support plate. The support plate and the manufactured needle were bonded to each other to provide the acicular body of Example 5. In the above adhesive tape, the brightness L* of the surface having the adhesive layer was 4.5 (measured in conformity with JIS K5600-4-5 (1999)).

EXAMPLE 6

(Manufacturing of Intaglio Plate)

The same intaglio plate as that of Example 1 was used.

(Preparation of Needle-Forming Solution)

The same needle-forming solution (hydroxypropyl cellulose solution) as that of Example 2 was used.

(Manufacturing of Needle)

The needle was formed in the same manner as Example 2.

The total light transmittance of the resultant needle measured in conformity with JIS K7105 (1981) was 30%.

(Manufacturing of Acicular Body)

An adhesive tape having an acrylic adhesive layer on the surface of a brown polyvinyl chloride base material was provided as a support plate. The support plate and the manufactured needle were bonded to each other to provide the acicular body of Example 6. In the above adhesive tape, the brightness L* of the surface having the adhesive layer was 4.0 (measured in conformity with JIS K5600-4-5 (1999)).

EXAMPLE 7

(Manufacturing of Intaglio Plate)

The same intaglio plate as that of Example 1 was used.

(Preparation of Needle-forming Solution)

The same needle-forming solution (hydroxypropyl cellulose solution) as that of Example 2 was used.

(Manufacturing of Needle)

The needle was formed in the same manner as Example 2.

The total light transmittance of the resultant needle measured in conformity with JIS K7105 (1981) was 30%.

(Manufacturing of Acicular Body)

An adhesive tape having an acrylic adhesive layer on the surface of a green polyvinyl chloride base material was provided as a support plate. The support plate and the manufactured needle were bonded to each other to provide the acicular body of Example 7. In the above adhesive tape, the brightness L* of the surface having the adhesive layer was 3.0 (measured in conformity with JIS K5600-4-5 (1999)).

In Examples 8, 9 and 10, colored needle-forming solution was used to form the base portion and the support plate of the needle.

EXAMPLE 8

(Manufacturing of Intaglio Plate)

The same intaglio plate as that of Example 1 was used.

(Preparation of Needle-Forming Solution (Needle))

The same needle-forming solution (chitosan succinamide solution) as that of Example 1 was used.

(Manufacturing of Needle)

The needle was formed in the same manner as Example 1 by using the needle-forming solution (needle). In so doing, squeezing was performed after the needle-forming solution was filled in the recesses of the intaglio plate so that the respective needles were independently formed. The total light transmittance of the resultant needle measured in conformity with JIS K7105 (1981) was 85%.

(Preparation of Needle-forming Solution (Support Plate))

Hydroxypropyl cellulose and edible pigment (black) were dissolved in ethanol to prepare hydroxypropyl cellulose solution with the hydroxypropyl cellulose concentration of 10 wt %.

(Manufacturing of Support Plate/Manufacturing of Acicular Body)

A spin coating method was used to fill the space in the recesses in which the needles are formed with the needle-forming solution (support plate). Then, the needle-forming solution was further supplied to such an extent that a layer was formed on the intaglio plate. The intaglio plate was heated at a temperature of 120° C. for a period of 10 minutes by using a heat source so that the needle-forming solution (support plate) was dried and solidified. A hotplate was used as the heat source.

After the solidifying process, the needle-forming solution which was solidified in the form of layer was held and removed from the intaglio plate to manufacture a two-layered acicular body having the support plate and the needle made of the needle-forming solution.

The brightness L* of the support plate was 1.5 (measured in conformity with JIS K5600-4-5 (1999)).

EXAMPLE 9

(Manufacturing of Intaglio Plate)

The same intaglio plate as that of Example 2 was used.

(Preparation of Needle-Forming Solution (Needle))

The same needle-forming solution (hydroxypropyl cellulose solution) as that of Example 2 was used.

(Manufacturing of Needle)

The needle was formed in the same manner as Example 8. The total light transmittance of the resultant needle measured in conformity with JIS K7105 (1981) was 40%.

(Preparation of Needle-forming Solution (Support Plate))

Pullulan and edible pigment (black) were dissolved in hot water at 45° C. to prepare pullulan solution with the pullulan concentration of 10 wt % as a needle-forming solution (support plate).

(Manufacturing of Support Plate/Manufacturing of Acicular Body)

A spin coating method was used to fill the space in the recesses in which the needles are formed with the needle-forming solution (support plate). Then, the needle-forming solution was further supplied to such an extent that a layer was formed on the intaglio plate. The intaglio plate was heated by using a heat source so that the needle-forming solution (support plate) was dried and solidified.

After the solidifying process, the needle-forming solution which was solidified in the form of layer was held and removed from the intaglio plate to manufacture a two-layered acicular body having the support plate and the needle made of the needle-forming solution.

The brightness L* of the support plate was 1.5 (measured in conformity with HS K5600-4-5 (1999)).

EXAMPLE 10

(Manufacturing of Intaglio Plate)

The same intaglio plate as that of Example 1 was used.

(Preparation of Needle-forming Solution (Needle))

The same needle-forming solution (chitosan succinamide solution) as that of Example 1 was used.

(Manufacturing of Needle)

The needle was formed in the same manner as Example 8. The total light transmittance of the resultant needle measured in conformity with JIS K7105 (1981) was 85%.

(Preparation of Needle-forming Solution (Support Plate))

Hydroxypropyl cellulose and methylene blue (blue pigment) were dissolved in ethanol to prepare hydroxypropyl cellulose solution with the hydroxypropyl cellulose concentration of 10 wt %.

(Manufacturing of Support Plate/Manufacturing of Acicular Body)

A two-layered acicular body having the support plate and the needle made of the needle-forming solution (support plate) was manufactured in the same manner as Example 8.

The brightness L* of the support plate was 4.0 (measured in conformity with JIS K5600-4-5 (1999)).

COMPARATIVE EXAMPLE 1

(Manufacturing of Intaglio Plate)

The same intaglio plate as that of Example 1 was used.

(Preparation of Needle-Forming Solution)

The same needle-forming solution (chitosan succinamide solution) as that of Example 1 was used.

(Manufacturing of Needle)

The needle was formed in the same manner as Example 1. The total light transmittance of the resultant needle measured in conformity with JIS K7105 (1981) was 80%.

(Manufacturing of Acicular Body)

An adhesive tape having an acrylic adhesive layer on the surface of a white polyvinyl chloride base material was provided as a support plate. The support plate and the manufactured needle were bonded to each other to provide the acicular body of Comparative example 1. In the above adhesive tape, the brightness L* of the surface having the adhesive layer was 9.0 (measured in conformity with JIS K5600-4-5 (1999)).

COMPARATIVE EXAMPLE 2

(Manufacturing of Intaglio Plate)

The same intaglio plate as that of Example 1 was used.

(Preparation of Needle-forming Solution (Needle))

The same needle-forming solution (chitosan succinamide solution) as that of Example 1 was used.

(Manufacturing of Needle)

The needle was formed in the same manner as Example 8. The total light transmittance of the resultant needle measured in conformity with JIS K7105 (1981) was 85%.

(Preparation of Needle-forming Solution (Support Plate))

Hydroxypropyl cellulose and edible pigment (white) were dissolved in ethanol to prepare the solution with the hydroxypropyl cellulose concentration of 10 wt % as a needle-forming solution (support plate).

(Manufacturing of Support Plate/Manufacturing of Acicular Body)

A two-layered acicular body having the support plate and the needle made of the needle-forming solution (support plate) was manufactured in the same manner as Example 8.

The brightness L* of the support plate was 9.0 (measured in conformity with JIS K5600-4-5 (1999)).

(Evaluation 1)

The acicular bodies of the Examples and Comparative examples were visually observed from a position on the needle-side with the needle overlapping the support plate.

In Examples 1 to 10, the needles were clearly visually observed. Further, the tips of the needles were visually observed as bright spots. In Comparative examples 1 and 2, the needles were not visually observed due to visible light reflection of the support plate.

(Evaluation 2)

The needles of the acicular bodies of the Examples and Comparative examples were peeled off from the artificial skin 10 minutes after the piercing and were visually observed from the same point as that of Evaluation 1.

In Examples 1 to 10, the bright spots, which were observed in Evaluation 1, were not observed. This revealed that the tips of the needles were dissolved. In Comparative examples 1 and 2, whether or not the tips of the needles were dissolved was not confirmed.

Figure 9:
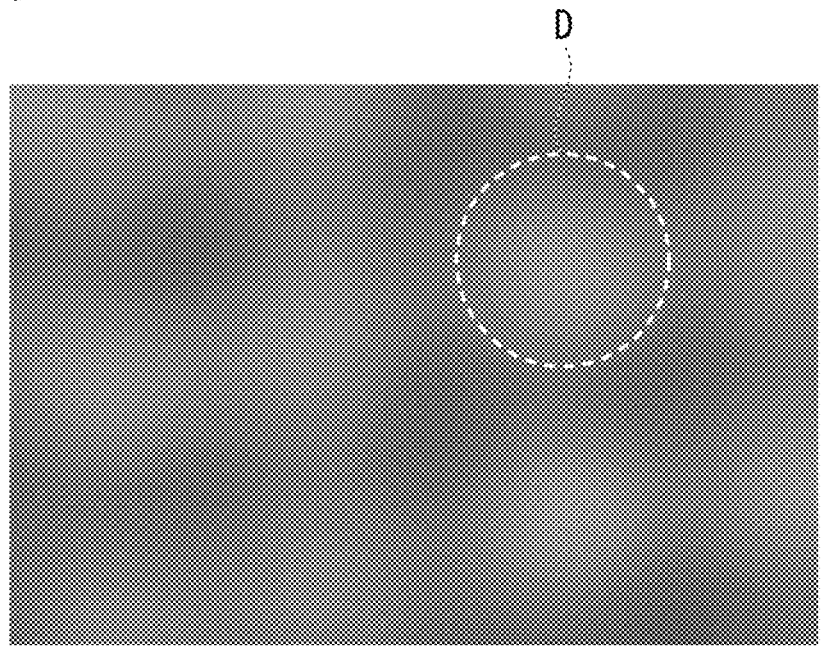
FIG. 9 is a microscope image of the acicular body of an example of the present invention taken from the needle-side.
Figure 10:
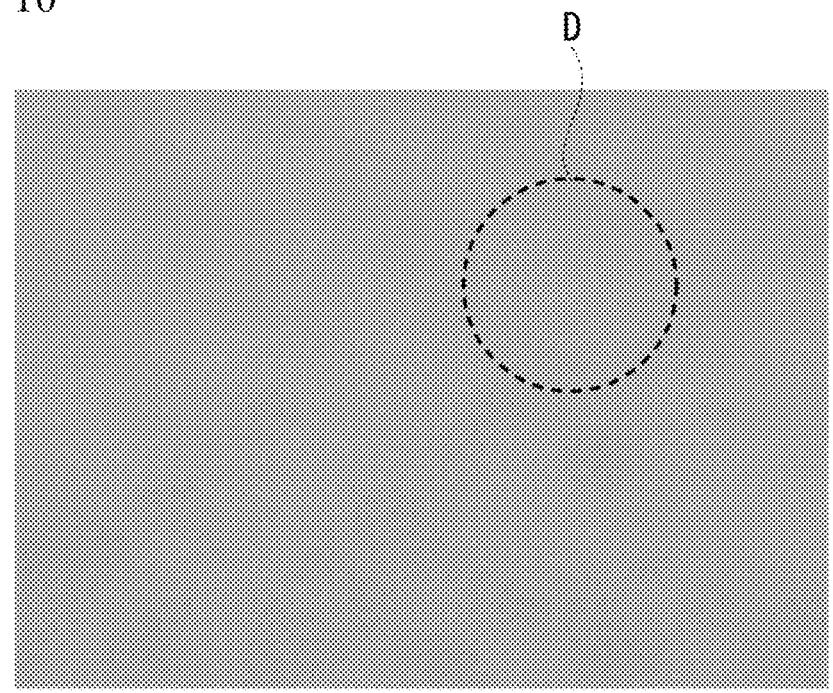
FIG. 10 is a microscope image of the acicular body of a comparative example taken from the needle-side.

FIG. 9 shows a microscope image of the acicular body according to Example 1 taken from the needle-side. FIG. 10 shows a microscope image of the acicular body of Comparative example 2 taken under the same condition as FIG. 9. In FIGS. 9 and 10, the needle is located within an area D surrounded by the dotted line. While the position of the needle was readily confirmed by visual observation in FIG. 9, the needle was not readily confirmed in FIG. 10.

Although the embodiments and examples of the present invention have been described, the technical scope of the present invention is not limited to those embodiments, and combinations of the components may be varied and various modifications and deletions can be made to the components without departing from the teachings of the present invention.

The acicular body which uses a biocompatible material made of water-soluble polymer such as chitosan, hydroxypropyl cellulose or collagen can dissolve in the skin after it is pierced into the skin. Accordingly, the acicular body can be manufactured to contain a substance to be delivered into the skin along with the water-soluble polymer so that the substance is delivered in the skin as the water-soluble polymer dissolves after the acicular body is pierced into the skin.

Further, an acicular body which uses a thermoplastic resin such as polycarbonate, cyclic olefin copolymer, polylactic acid or polyglycolic acid can be manufactured with the surface of the acicular body being coated with a solution of substance to be delivered so that the substance is delivered in the skin after it is pierced into the skin.

In piercing the acicular body into the skin, an adhesive material is preferably provided on the surface of the acicular body to improve adhesion to the skin. A colorless transparent adhesive is used to improve the appearance of the acicular body pierced into the skin.

However, there is a problem that, when the acicular body formed of a combination of a colorless transparent adhesive and a substantially colorless transparent acicular body made of hydroxypropyl cellulose or the like is pierced into the skin and then peeled off from the skin after dissolution of the acicular body, a clinician or a patient can not easily confirm by visual observation to what extent the needles remain on the acicular body which has been peeled off from the skin and thus whether the needles will be sufficiently dissolved in the skin or not.

In light of the above circumstances, the present invention has an object of providing an acicular body which allows for easy visual observation of the appearance of the needle.

An acicular body according to an aspect of the present invention includes a support plate having a brightness of 5.0 or less; and a needle disposed on the support plate, the needle including a tip which is formed so as to pierce the skin and a light transmission area which is located in an area containing the tip and has a total light transmittance of 20% or more.

The needle according to an embodiment of the present invention may be made of a chitosan derivative.

The needle according to an embodiment of the present invention may be made of a water-soluble material.

The needle according to an embodiment of the present invention may include a base portion having a surface which faces a surface of the support plate.

The support plate according to an embodiment of the present invention may include a projection formed at a position which corresponds to the needle.

The support plate according to an embodiment of the present invention may be made up of a transparent adhesive layer and a colored base material tape.

The support plate according to an embodiment of the present invention may include a colored base material tape and a transparent adhesive layer disposed on the base material tape.

According to the above aspect of the present invention, the appearance of the needle can be easily confirmed by visual observation.

REFERENCE SIGNS LIST

1 acicular body
10, 11, 40, 60 support plate
10*b* projection
20 needle
20*a* tip
20*b* base portion (needle)
20*c* light transmission area
12 adhesive layer
50 base material tape Obviously, numerous modifications and variations of the present invention are possible in light of the above teachings. It is therefore to be understood that within the scope of the appended claims, the invention may be practiced otherwise than as specifically described herein.

What is claimed is:

1. An acicular body, comprising:
    a support plate having a color such that the color has a brightness L* of 5.0 or less as measured in conformity with JIS K5600-4-5 of 1999; and
    at least one needle formed on the support plate and including a needle tip portion formed to pierce a skin,
    wherein the at least one needle has a total light transmittance of 20% or more such that the at least one needle is transparent or translucent for visible observation of the color of the support plate via the at least one needle, and the support plate is formed such that the needle tip portion of the at least one needle is visually observed against the support plate.

2. The acicular body according to claim 1, wherein the at least one needle comprises a chitosan derivative.

3. The acicular body according to claim 2, wherein the at least one needle has a total light transmittance of 30% or more.

4. The acicular body according to claim 2, wherein the at least one needle has a total light transmittance of 40% or more.

5. The acicular body according to claim 2, wherein the at least one needle has a total light transmittance of 80% or more.

6. The acicular body according to claim 2, wherein the at least one needle has a total light transmittance of 85% or more.

7. The acicular body according to claim 1, wherein the at least one needle comprises a water-soluble material.

8. The acicular body according to claim 1, wherein the at least one needle includes a base portion having a surface which faces a surface of the support plate.

9. The acicular body according to claim 8, wherein the support plate includes a colored base material tape and a transparent adhesive layer formed on the colored base material tape, and the at least one needle includes a plurality of needles arrayed on the base portion.

10. The acicular body according to claim 1, wherein the support plate includes a projection formed at a position which corresponds to the at least one needle.

11. The acicular body according to claim 1, wherein the support plate includes a colored base material tape and a transparent adhesive layer formed on the colored base material tape.

12. The acicular body according to claim 11, wherein the at least one needle has a total light transmittance of 30% or more.

13. The acicular body according to claim 11, wherein the at least one needle has a total light transmittance of 40% or more.

14. The acicular body according to claim 11, wherein the at least one needle has a total light transmittance of 80% or more.

15. The acicular body according to claim 11, wherein the at least one needle has a total light transmittance of 85% or more.

16. The acicular body according to claim 1, wherein the at least one needle has a total light transmittance of 30% or more.

17. The acicular body according to claim 1, wherein the at least one needle has a total light transmittance of 40% or more.

18. The acicular body according to claim 1, wherein the at least one needle has a total light transmittance of 80% or more.

19. The acicular body according to claim 1, wherein the at least one needle has a total light transmittance of 85% or more.

20. The acicular body according to claim 1, wherein the at least one needle includes a plurality of needles arrayed on the support plate.

* * * * *